United States Patent [19]

Sinko et al.

[11] Patent Number: 5,195,513
[45] Date of Patent: Mar. 23, 1993

[54] INFANT PALATE PROTECTIVE PROSTHESIS

[75] Inventors: George E. Sinko; Charles A. Jones, both of San Antonio, Tex.

[73] Assignee: Gesco International, Inc., San Antonio, Tex.

[21] Appl. No.: 907,845

[22] Filed: Jul. 2, 1992

[51] Int. Cl.[5] .......................................... A61M 16/00
[52] U.S. Cl. ........................ 128/200.26; 128/207.14; 604/79
[58] Field of Search ................ 623/9; 604/77, 79; 128/200.26, 207.14, 207.17

[56] References Cited

U.S. PATENT DOCUMENTS

| | | | |
|---|---|---|---|
| 3,927,676 | 12/1975 | Schultz | 128/207.17 |
| 4,112,936 | 9/1978 | Blachly | 128/207.14 |
| 4,223,671 | 9/1980 | Muto | 128/200.26 |
| 4,270,529 | 6/1981 | Muto | 128/200.26 |
| 4,270,531 | 6/1981 | Blachly et al. | 128/207.14 |
| 4,338,930 | 7/1982 | Williams | 128/200.26 |
| 4,548,200 | 10/1985 | Wapner | 128/207.17 |
| 4,906,234 | 3/1990 | Voychehovski | 604/79 |

OTHER PUBLICATIONS

Cinoza, et al., "Prevention of palatal groove formation in premature neonates requiring intubation," Journal of Pediatrics, vol. 115, #1, pp. 133–135, 1989.

*Primary Examiner*—Randy C. Shay
*Attorney, Agent, or Firm*—Cox & Smith Incorporated

[57] ABSTRACT

A prosthesis for protecting the palate of a small infant from injury by airway or other tubes required to be maintained in the throat of an infant patient for extended periods, comprises a thin mass of injection molded, soft, resiliently deformable plastic having an upper surface contoured to conform to a normal palate of a healthy infant of approximately the same size as the patient. The plastic mass incorporates an integral, downwardly opening passage for an air way tube, thus disposing the plastic mass between the tube and the palate of the infant patient.

5 Claims, 2 Drawing Sheets

INFANT PALATE PROTECTIVE PROSTHESIS

BACKGROUND OF THE INVENTION

1. Field of the Invention

This invention relates to a palate protective prosthesis for holding endotracheal, orotracheal or feeding tubes utilized for low birth weight neonates suffering respiratory distress or other illness requiring insertion of a tube down the trachea.

2. Summary of the Prior Art

Some infants, and particularly low birth weight neonates, often require prolonged orotracheal intubation to combat respiratory distress. A frequent complication of prolonged intubation is the formation of a palatal groove caused by pressure, and movement from the orotracheal tube against the palate and within the trachea. Ventilators may cause constant movement and vibration which also tends to cause a tube to rub on the palate, back and forth. In neonatal infants in particular, the palate has not developed sufficient hardness to resist the pressure and movement produced by the orotracheal tube over a prolonged period, and the result is the formation of a substantial permanent groove in the palate, with the resulting possible consequences of problems with dentition, speech, hearing, and middle ear disease.

Several forms of supports for orotracheal tubes have heretofore been developed for use primarily with adults. A common form of such prior art devices is characterized by the term "bite block" because generally the securement of the orotracheal tube is accomplished by a support member positioned between the patient's upper and lower teeth. The use of any such support with an infant, and particularly a neonatal infant, is obviously impractical.

An approach for protecting neonatal infants against the formation of a palatal groove is described in Volume 115, #1, pages 133-135 of the Journal of Pediatrics. In this article, the procedure followed was the formation of a maxillary impression of the palate and then the fabrication of a palate guard from a cast of the initial impression. The result was a rigid "palate plate" which, as stated in the article, required replacement of the prosthesis after four to six weeks of use, depending on the infant patient's growth rate.

This approach resulted in a significant reduction in the formation of palatal grooves due to pressure from the orotracheal tube; but, obviously involved substantial expense due to the necessity of having a skilled dentist take an impression and make an appropriate cast to form a new prothesis every four to six weeks. Moreover, the accuracy of the prothesis conformity to the palate of the infant is always in question due to the very small mouth opening within which the impression had to be made, generally using only the little finger for neonatal infants. Since the dental cast palate plate is rigid, the relatively soft infant palate may be deformed to conform to an inaccurate cast, thus creating a maldeformed palate in the infant patient.

With this background, it is readily apparent that an improved, low cost prosthesis is needed for the protection of the palates of infants requiring intubation, and not involving dental casts made from maxillary impressions taken in the mouth of the infant patient.

SUMMARY OF THE INVENTION

This invention contemplates the formation of an infant palatal protective prosthesis from an injection moldable plastic material having the characteristic of being soft and readily resiliently deformable. Thus, a thin mass of a suitable plastic is molded into a configuration having a soft, resilient upper surface approximately matable with the palate of the palate surface of the infant patient. Such mass may be said to be in the form of a thin disc having an arcuate forward wall portion and a generally linear rear wall portion. The upper surface of the thin mass of plastic is molded to conform to the palate configuration of an infant of approximately the same size as the infant patient. Around the forward and sides of the molded mass of plastic, an integral, upstanding ridge is provided which is contoured so as to conform to the inner surfaces of the upper gum.

Putting a palatal conforming prosthesis having typical contours and dimensions in the mouth of a specific infant results in contact and non contact areas of the upper surface of the plastic mass with the surface of the patient's palate. The non contact areas are, however, minimized due to the fact that the soft, resilient nature of the plastic mass is such that the slight upward pressure normally exerted by an oral- tracheal or other airway tube, will resiliently depress the contact areas of the plastic mass to maintain the entire upper surface of the plastic mass in snug engagement with the palate and the surrounding inner wall surface of the upper gum of the infant patient. Thus, concentration of upward forces on a limited area of the palate is minimal.

The plastic mass is provided at its forward arcuate portion with an integral radial projection which defines a passageway for an orotracheal or other airway tube. Preferably, this passageway is in the form of a downwardly opening channel formed in the aforementioned radial projection and the orotracheal tube may be conveniently secured to the plastic mass by adhesive tape wrapped around the projection and engaging the bottom surfaces of the tube. To prevent slippage of the adhesive tape, the integral projection on the plastic mass is preferably provided with an outwardly projecting shoulder around the outer end of the integral projection, thus providing a channel for the tube securing tape.

Any form of conventional tube holding apparatus may be employed to position and hold the orotracheal tube on the head of the infant. Preferably the same adhesive tape that secures the airway tube to the prosthesis may also secure the tube to the head of the patient.

Further objects and advantages of the invention will be readily apparent to those skilled in the art from the following detailed description, taken in conjunction with the annexed sheets of drawings, on which is shown a preferred embodiment of the invention.

DESCRIPTION OF PREFERRED EMBODIMENT

Figure 1:
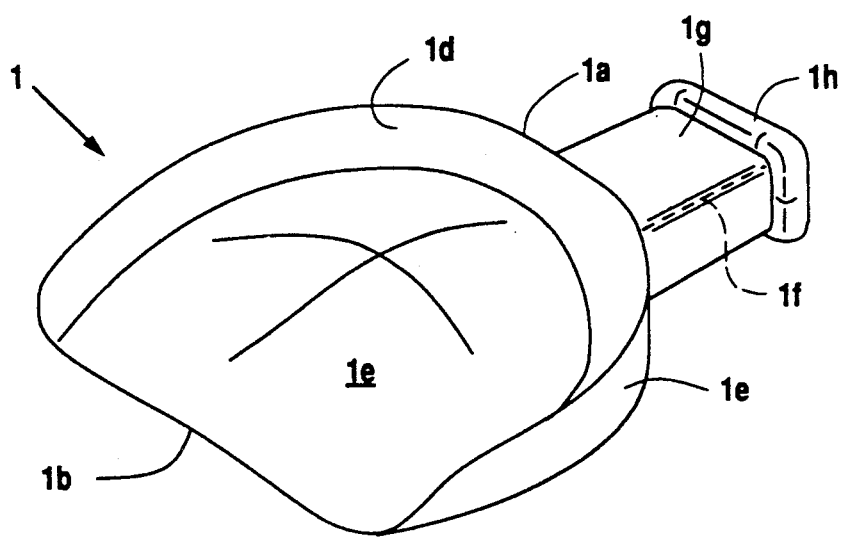
FIG. 1 is an enlarged scale perspective view of a palate protective prothesis embodying this invention.
Figure 2:
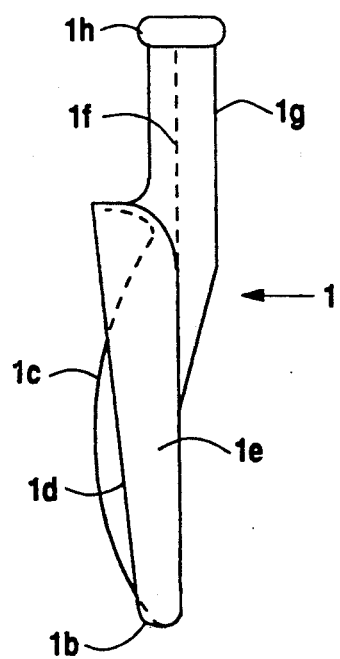
FIG. 2 is a side elevational view of FIG. 1.

Referring to FIGS. 1 and 2, a palatal protective prosthesis 1 embodying this invention comprises a thin mass of injection moldable material having a forward arcuate portion 1a having a curvature corresponding to that of the upper gum of an infant of approximately the same size as the infant patient. The rear end 1b of the prosthesis has a substantially linear configuration.

The upper surface 1c of the prosthesis 1 is slightly domed and molded to a configuration which conforms to the palate surface of said infant of approximately the same size as the infant patient. Around the forward and rear sides of the prosthesis 1, an integral upstanding rib 1d is formed having an outer surface 1e which would conform to the inner surfaces of the upper gum of an infant approximately the same size as the infant patient.

An integral forward projection 1g is molded to the arcuate forward end 1a of the prothesis 1 and defines a downwardly opening channel 1f within which an orotracheal tube or other airway may be snugly inserted. The projection 1g is preferably formed with an outwardly projecting shoulder or abutment 1h on its extreme forward end to define a channel for receiving adhesive tape 3 which is wrapped around the projection 1g and engages the bottom surface of the airway tube 2, as best illustrated in FIG. 4.

The material employed to form the prosthesis 1 is preferably a medical grade soft silicone. While this material is soft, it is resiliently deformable and not plastically deformable. A soft plastically deformable material, having no resilience against deformation would not be satisfactory, because the slight pressure applied to any portion of the plastically deformable material while inserting the same in the infant's mouth would result in a non-conformity of the plastic prothesis to the internal contour of the palate and upper gum of the infant patient. More importantly, with prolonged intubation, the pressure of the airway tube would form a groove in the prothesis and then in the palate. Other resiliently deformable soft plastics, such as medical grade vinyls, may be utilized but the medical grade soft silicone material is preferred.

Figure 3:
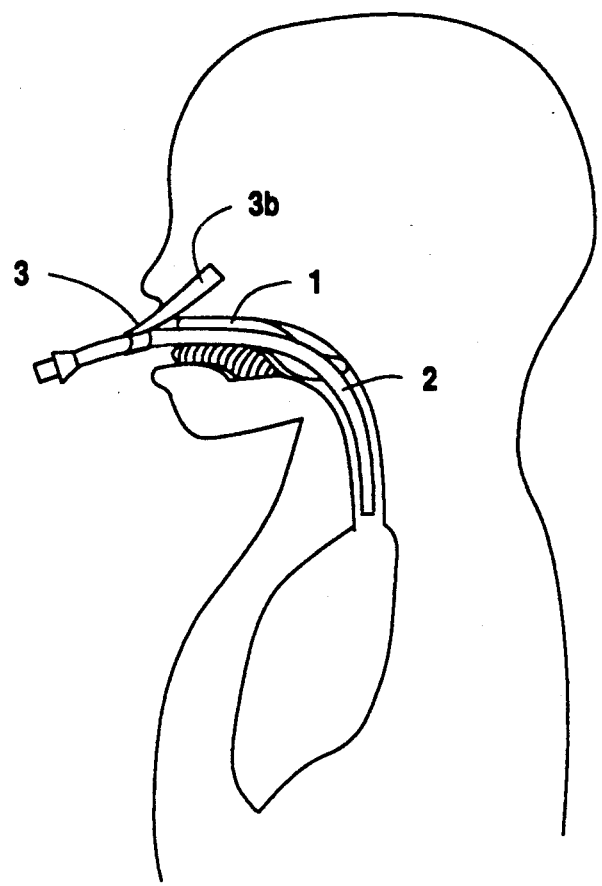
FIG. 3 is an enlarged scale schematic view illustrating the positioning of the prosthesis in the mouth of an infant and an airway tube secured to the prosthesis.
Figure 4:
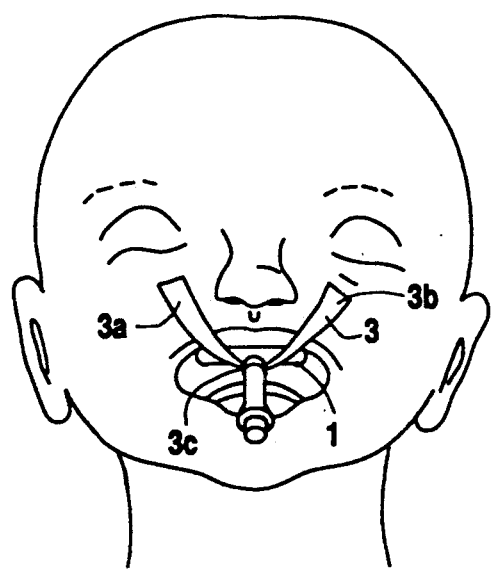
FIG. 4 is an enlarged scale sectional view illustrating the securement of an airway tube to the palate protective prosthesis and to the infant patient.

Referring to FIGS. 3 and 4, the airway tube 2 is inserted into the throat. The protective prothesis 1 is inserted into the mouth of the infant patient and then engaged with the airway tube 2. The airway tube 2 is then secured to the prosthesis 1 by adhesive tape 3. The airway tube 2 is suitably secured to the head of the infant so as to exert a slight upward pressure on the plastic prosthesis 1, thus causing the soft resiliently deformable material of the prothesis to conform to the palate and the inner surfaces of the upper gum of the infant patient in the manner illustrated in FIG. 3. Any inaccuracies of the prothesis in exactly conforming to the palate of the infant patient, resulting in contacting and non-contacting areas of the prothesis, are overcome by the resilient deformation of the soft, resiliently deformable protective prothesis 1.

The outer portions of the airway tube 2 may be supported on the head of the patient by any conventional means. Prior art tube holding devices are shown in U.S. Pat. Nos. 4,223,671, 4,270,529, and 4,906,234. Preferably the same adhesive tape 3 that secures the airway tube 2 to the prothesis may also secure the airway tube 2 and prothesis to the face of the patient. Thus the length of adhesive tape 3 may have its medial portion 3c wrapped around the projection 1g and the airway tube 2, and the free ends 3a and 3b secured to opposite sides of the infant's face.

By molding the plastic prothesis 1 to conform to the typical configuration of a mouth of an infant of the same approximate size as the infant patient, the amount of non-contacting areas on the prothesis when inserted into the mouth of the infant patient is significantly reduced.

Because the plastic prothesis embodying this invention is obviously very economical to manufacture, a substantial number of sizes of the prothesis can be provided at minimum cost. Dental casts are made from impressions taken from healthy infants of progressive sizes. Such dental casts are utilized to produce the palate and upper gum defining surfaces of an injection mold.

Thus, the particular prothesis to be used in an infant patient is determined by the size relationship of the infant patient to infant of similar size whose palate was used to shape the palate and upper gum defining surfaces of the injection mold. As the infant patient progresses and grows, a larger size plastic prothesis, produced from a mold derived from a larger infant, can be substituted for the one initially used. Thus, the growth of the infant requires no significant expense to the hospital to provide new, larger plastic prostheses. This is in distinct contrast to the existing procedure utilizing dental casts made by a dentist from an impression taken in the hospital. Moreover, the palate protective prothesis embodying this invention cannot produce grooves or impressions in the palate due to lack of exact conformity of the upper surface of the prothesis with the surfaces of the palate or the upper interior gums. Thus, the plastic prothesis embodying this invention provides not only economic but significant medical benefits for the infant patient.

What is claimed and desired to be secured by Letters patent is:

1. Apparatus for protecting the palate of an infant patient from harmful pressure of an airway tube passing through the mouth comprising:
    a thin mass of soft, resiliently deformable plastic having an arcuate forward portion approximating the curvature of the upper gum of the infant patient;
    said mass having a molded upper surface conforming to the normal contour of the palate of an infant of the same approximate size as the infant patient;
    said molded upper surface being readily resiliently compressible to conform to the palate of the infant patient;
    an upstanding rim integrally formed on said arcuate forward portion of said mass and engagable with the inner surface of the upper gum of the infant patient to position said mass in the infant patient's mouth; and
    an integral, generally radial projection formed on said arcuate forward portion of said mass;
    said projection defining a passage for receiving an airway tube and thereby positioning said mass intermediate said airway tube and the infant patient's palate.

2. The apparatus of claim 1 wherein said mass is formed of a medical grade silicone material.

3. The apparatus of claim 1 wherein said passage comprises a downwardly open channel for receiving said airway tube.

4. The apparatus of claim 3 further comprising an external peripheral shoulder on a forward end of said projection, thereby defining a recess to accommodate a band of adhesive tape to secure the airway tube in said channel.

5. The apparatus of claim 1 further comprising adhesive tape having one portion wrapped around said projection and engageable with the airway tube, and end portions engagable with opposite sides of the head of the infant patient.

* * * * *